(12) United States Patent
Messing

(10) Patent No.: US 6,611,699 B2
(45) Date of Patent: Aug. 26, 2003

(54) CATHETER WITH AN IRRIGATED COMPOSITE TIP ELECTRODE

(75) Inventor: Katie Messing, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/896,730

(22) Filed: Jun. 28, 2001

(65) Prior Publication Data

US 2003/0004506 A1 Jan. 2, 2003

(51) Int. Cl.[7] .............................. A61B 5/04; A61B 18/18
(52) U.S. Cl. ......................... 600/372; 600/373; 606/49
(58) Field of Search .............................. 600/372, 373, 600/374, 381, 395; 606/41, 45, 46, 49, 77, 48, 50

(56) References Cited

U.S. PATENT DOCUMENTS

| | | | | |
|---|---|---|---|---|
| 3,596,662 A | * | 8/1971 | Bolduc | 174/69 |
| 5,437,662 A | * | 8/1995 | Nardella | 606/38 |
| 5,688,267 A | * | 11/1997 | Panescu et al. | 606/31 |
| 5,836,947 A | * | 11/1998 | Fleischman et al. | 606/41 |
| 5,902,328 A | * | 5/1999 | LaFontaine et al. | 600/373 |
| 6,017,338 A | * | 1/2000 | Brucker et al. | 606/122 |
| 6,032,077 A | * | 2/2000 | Pomeranz | 607/101 |
| 6,053,912 A | * | 4/2000 | Panescu et al. | 606/31 |
| 6,099,524 A | | 8/2000 | Lipson et al. | |
| 6,129,724 A | * | 10/2000 | Fleischman et al. | 606/41 |

* cited by examiner

Primary Examiner—Linda C. M. Dvorak
Assistant Examiner—Kenneth Schopfer
(74) Attorney, Agent, or Firm—Bingham McCutchen LLP

(57) ABSTRACT

Various catheter designs with irrigated tip electrodes are provided for reducing the heating of the tip resulting from RF biasing. The electrode tip of the catheter may be comprised of a highly thermal conductivity layer covered by a biologically compatible material and having irrigation or irrigation channels for removing excess thermal energy from the catheter tip and the surrounding area of the catheter tip. The catheter tip may be designed with multiple irrigation channels, multiple channel pathways, and/or exterior shapes to improve the cooling of the tip. These approaches may be used individually or in combination to produce a catheter tip with improved heat dissipation characteristics.

25 Claims, 4 Drawing Sheets

CATHETER WITH AN IRRIGATED COMPOSITE TIP ELECTRODE

TECHNICAL FIELD

The present invention generally relates to catheters. More specifically, the present invention relates to an improved catheter that may be used in mapping and ablation procedures of biological tissues.

BACKGROUND OF THE INVENTION

For many years, catheters have had widespread application in the medical field. For example, mapping and ablation catheters have been extensively used in the treatment of cardiac arrhythmia. Cardiac arrhythmia treatments help restore the normal operation of the heart in pumping blood to the body. Mapping and ablation catheters play a critical role in these highly delicate treatments.

Typically, the catheters used in mapping and ablation procedures are steerable electrophysiological ("EP") catheters that may be precisely positioned anywhere in the heart. These catheters are generally used during two distinct phases of treatment for heart arrhythmia. In one phase of treatment, the catheters are used to map the heart by locating damaged tissue cells. This involves the locating of damaged cells by steering the catheter to selected locations throughout the heart and detecting irregularities in the propagation of electrical wave impulses during contraction of the heart (a procedure commonly referred to as "mapping"). During the other phase of treatment, the same catheters are typically used to create scarring lesions at the location where damaged cells have been found (a procedure commonly referred to as "ablation").

Ablation procedures using EP catheters are typically performed using radio frequency ("RF") energy. In this regard, an EP catheter has one or more ablation electrodes located at its distal end. The physician directs energy from the electrode through myocardial tissue either to an indifferent electrode, such as a large electrode placed on the chest of the patient (in a uni-polar electrode arrangement), or to an adjacent electrode (in a bipolar electrode arrangement) to ablate the tissue. Once a certain temperature has been attained, resistance heating of the tissue located adjacent the one or more electrodes occurs, producing lesions at the targeted tissue.

Referring to FIG. 1, a conventional catheter that may be used in mapping and ablation procedures is provided. FIG. 1 shows the distal end of a catheter. The catheter distal end comprises a body member 170, for example, a plastic tubing, and an electrode tip 160, attached to the distal end of the body member 170. A RF wire 150 runs through an irrigation channel 110, or alternatively through a separate lumen formed within the body member 170, and is connected to the electrode tip 160. At the distal end of the electrode tip 160 is a sensor 140, for example, a thermistor or a thermocouple, which is in thermal contact with the electrode tip 160. A sensor wire 145 extends from the sensor 140 back through the irrigation channel 110, or alternatively through a separate lumen formed within the body member 170. Ring electrodes 90 may be mounted around the body member 170. The electrode tip 160 is used to provide RF energy to heart tissues during ablation procedures. The RF wire connects the electrode tip 160 to a RF power supply (not shown). The ring electrodes 90 may be used together with the electrode tip 160 for mapping procedures.

Conventional catheters, such as those used for mapping and ablation procedures, are typically made entirely from a biologically compatible material, for example, a platinum iridium alloy (90 percent/10 percent). In general, however, the thermal conductivity of a platinum iridium alloy is not as high as that of other materials, such as copper or gold. One possible approach to increasing the thermal conductivity of an electrode is to form it from a material that is both biologically compatible and highly thermally conductive. However, many materials that are both biologically compatible and have highly thermal conductivity characteristics, such as gold, tend to be expensive.

As a result, catheter tips made entirely from economically feasible materials may be inefficient at dissipating excess thermal energy, thus creating thermal issues. Specifically, when excessive thermal energy is applied to a catheter electrode during ablation procedures, blood protein and other biological tissue may coagulate on the electrode, creating an embolic hazard. Such build up of coagulant on the electrode also hinders the transmission of RF energy from the electrode into the target tissue, thereby reducing the effectiveness of the ablation procedure. Ideally, it would be preferable to be able to focus the RF energy entirely on the targeted heart tissues without damaging the surrounding tissues or blood cells. That is, it would be highly preferable to be able to generate a good size lesion at a specifically defined area without altering, damaging, or destroying other surrounding tissue or blood.

In addition, it is generally desirable to be able to minimize the amount of time it takes to complete an ablation procedure. Typically, the longer it takes to complete an ablation procedure, the greater the health risk to the patient. Unfortunately, the time it takes to perform an ablation procedure may be related to how much thermal energy is directed towards the targeted tissue. That is, the greater the thermal energy directed towards the targeted tissue, the quicker the procedure can be performed. However, the amount of thermal energy that may be applied to the targeted tissue may be limited by damage that may potentially occur to the surrounding blood cells and tissues at highly thermal energy levels. For the above reasons, an EP catheter that is able to efficiently dissipate excess heat would be highly desirable.

SUMMARY OF THE INVENTION

The present inventions are directed to medical ablation electrodes that are capable of more efficiently dissipating heat during an ablation procedure.

In accordance with a first aspect of the present inventions, a medical ablation electrode comprises a biologically compatible outer layer, e.g., platinum iridium alloy, and a thermally conductive inner layer, e.g., copper. An irrigation channel is in contact with the inner layer for channeling cooling fluid. Preferably, the inner layer is in contact with the outer layer, e.g., by plating the outer layer onto the inner layer. In this manner, the conductive inner layer provides a highly conductive medium for increased heat dissipation from the electrode surface and its surrounding space, to an irrigating fluid flowing through the irrigation channel. The irrigating fluid then quickly removes the heat from the electrode during a heating operation, for example, during ablation.

In accordance with a second aspect of the present inventions, a medical ablation electrode comprises a thermally conductive proximal section having a substantially distally facing wall, and an irrigation channel formed within the proximal section for channeling cooling fluid. The electrode further comprises a thermally conductive distal section and one or more irrigation exit ports that extend through the distally facing wall of the proximal section. Thus, when cooling fluid is conveyed through the irrigation channel, it flows out through the exit ports over the exterior surface of the distal section, dissipating heat from the electrode.

In accordance with a third aspect of the present inventions, a medical ablation electrode comprises a thermally conductive housing having one or more concave sections and one or more convex sections, an irrigation channel formed within the housing for channeling cooling fluid, and one or more irrigation exit ports adjacent the one or more concave sections of the housing. In this manner, cooling regions are provided between the concave sections and the tissue to be ablated during the ablation process, whereby cooling fluid conveyed out of the exit ports from the irrigation channel enters the cooling areas to cool the tissue.

In accordance with a fourth aspect of the present inventions, a medical ablation electrode comprises a spiral-shaped thermally conductive irrigation tube having an irrigation channel. In this manner, the area of the irrigation channel exposed to the cooling fluid is maximized. In this case, the housing may form a single unitary structure that can be composed essentially of a biologically compatible material, which otherwise may not be feasible absent the additional cooling of the electrode.

In accordance with a fifth aspect of the present inventions, a medical ablation electrode comprises a thermally conductive rigid housing and one or more flow-through channels formed by an external surface of the rigid housing for channeling biological fluids over the external surface. As a result, the external surface of the rigid housing is increased by use of the flow-through channels.

In accordance with a sixth aspect of the present inventions, a medical ablation electrode comprises an inner cylinder having an inner irrigation channel extending therethrough for channeling cooling fluid. The electrode further comprises an outer cap that is mounted in a concentrically overlapping arrangement with the inner cylinder, such that an annular irrigation channel is formed between an inner surface of the outer cap and an outer surface of the inner cylinder for channeling the cooling fluid. In this manner, the cooling fluid flows over the inner and outer surfaces of the inner cylinder, thereby maximizing thermal dissipation of the heat into the cooling fluid. In a preferred embodiment, the inner cylinder and outer cap are composed of a thermally conductive biologically compatible material, and are mounted to each other using a pin. The electrode can further include one or more irrigation exit ports that are in fluid communication with the annular irrigation channel.

In accordance with a seventh aspect of the present inventions, a medical ablation electrode comprises a thermally conductive housing, and an irrigation channel formed in the housing for channeling cooling fluid. The housing in thin-walled, i.e., the wall of the housing has a thickness that is less than the diameter of the irrigation channel divided by the number 2. In this manner, the heat transfer rate through the housing wall in increased, thereby increasing the amount of thermal energy dissipated into the cooling fluid.

Thus, as can be seen, that in accordance with the second through seventh aspects of the present inventions, the electrode structure can be composed essentially of a biologically compatible material, which otherwise may not be feasible absent the additional cooling of the electrode and/or tissue. Alternatively, however, the housing can be composed of a highly thermally conductive inner layer and biologically compatible outer layer, or can be composed purely of a highly thermally conductive, but biologically compatible material, such as gold, to further increase the cooling of the electrode.

DESCRIPTION OF THE PREFERRED EMBODIMENTS

The present invention is directed towards a catheter device having a biologically compatible irrigated tip electrode. Such catheters may be used in, for example, mapping and ablation procedures of the human heart.

In a preferred embodiment of the present invention a catheter with an efficiently cooled tip is provided. Efficient cooling of a catheter tip electrode is achieved by combining two techniques for improving the cooling efficiency of the electrode. First, the electrode is constructed using components that have highly thermal conductivity and are compatible with biological fluids and tissues. Specifically, the electrode is composed of components that are made from highly conductive but non-biologically compatible materials that are encased or covered with a layer of biologically compatible material, e.g., a composite tip. By using highly thermal conductivity materials to construct the electrode, the thermal energy that may build up on the surface of the electrode and the surrounding area (where blood and tissue may be present) may be quickly dissipated. The electrode is also irrigated such that the heat present at the tip is quickly and efficiently carried away from the tip (two exemplary ways to irrigate an electrode will be discussed below—"internal irrigation" and "flushing irrigation".

Figure 1:
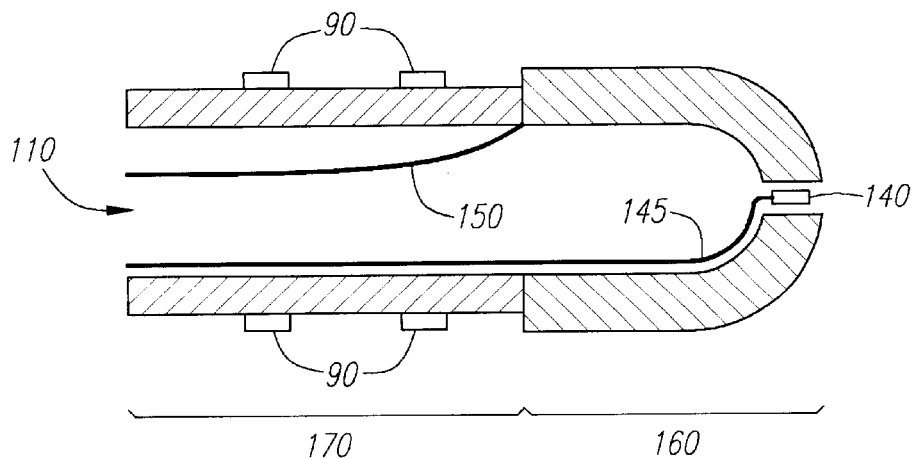
FIG. 1 is a cross-sectional view of a conventional catheter tip electrode used for mapping and ablation procedures.
Figure 2:
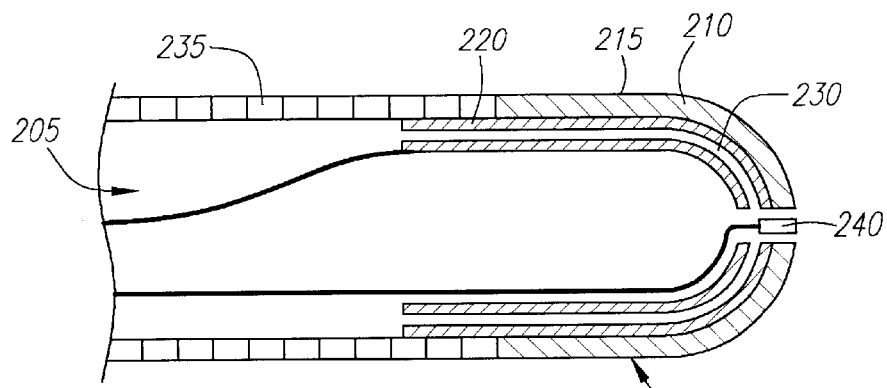
FIG. 2 is a cross-sectional view of an internally irrigated catheter tip electrode comprising a biologically compatible outer layer and a thermally conductive inner layer.

Referring now to FIG. 2, one embodiment of a catheter incorporating the principles of the present invention is illustrated. The catheter is shown comprising a catheter tip electrode 260 that includes a biologically compatible outer layer 210 and a highly thermal conductivity inner layer 220.

A temperature sensor 240, for example, a thermistor or a thermocouple, may be located at the distal end of the electrode 260. Other sensors, such as a 3D sensor (not shown), may also be placed at the distal end of the electrode 260. The biologically compatible outer layer 210 may be, for example, 90 percent platinum/10 percent iridium alloy. The outer layer 210 may, of course, be made from biologically compatible material other than a platinum iridium alloy. For example, gold and gold alloys, platinum and platinum alloys, titanium, tungsten, stainless steel, etc. may also be used for the outer layer. The highly thermal conductivity inner layer 220 may be, for example, pure copper, silver, or a copper or silver alloy. Other highly thermal conductivity materials other than copper or silver may be used for the inner layer. The proximal end of the inner layer 220 is exposed, such that the distal end of a catheter tube 235 can be bonded thereto.

The outer layer 210 may be thin, for example, in the range of microns, and may be placed over the inner layer 220 by, for example, plating techniques. Alternative methods of forming the tip may also be used. Preferably, the technique provides a good thermal and electrical connection between the outer layer 210 and inner layer 220. Details on general composite catheter tip electrodes are disclosed in U.S. Pat. No. 6,099,524 issued to Lipson et al., which is hereby expressly incorporated by reference as if fully set forth herein.

For purposes of irrigation, an irrigation channel 230 runs through the inner layer 220 to provide a flow path for irrigating fluids such as saline. The irrigation channel 230 is in fluid communication with an irrigation lumen 205, which extends proximally through the catheter tube 235 to a suitable pump (not shown). The irrigation channel 230 can be formed using any suitable method, such as machining or wax molding. As the irrigating fluid flows through the irrigation channel 230, it removes the heat being dissipated by the inner layer 220. For example, when the catheter of FIG. 2 is used in ablation procedures, excess heat may build up at the outer layer surface 215 and in the surrounding space (which may include blood and tissue). The excess heat will readily transfer through the highly conductive inner layer 220 and dissipate into the irrigating fluid flowing through the irrigation channel 230. The temperature and flow rate of the irrigating fluid can be of any suitable value, e.g., in the range of 30° C.–33° C., or alternatively room temperature, and 30–40 cc/min, or even lower, respectively.

By using an electrode with a core material (e.g., inner layer 220) that has highly thermal conductivity, several advantages may be realized. For example, the use of a highly conductive inner (core) material may result in a more efficient dissipation of heat energy, thus requiring a lower flow rate for the irrigating fluid. A lower flow rate would benefit the system because lower pump pressure would be required. This may thus lower the cost of the fluid pump, which is used to set the flow rate. A low flow rate decreases the chance of catheter failure due to lower pressure, thus making the catheter more safe for the patient. Also, because of improved heat dissipation, an irrigation fluid having higher temperature may be used. This will eliminate or reduce the need to cool the irrigation fluid temperature. For example, under the same power settings during ablation, the flow rate of the irrigating fluid may be lower than a tip made from a less conductive biologically compatible material. Furthermore, the present invention provides an irrigated catheter that delivers more power to the targeted tissue during ablation procedure without the need for increasing the flow rate of the irrigating fluid, thereby improving its efficiency at producing lesions.

The method of cooling the electrode 260 with an internal irrigation channel illustrated in FIG. 2 is commonly referred to as "internal irrigation". In internal irrigation, the irrigating fluid will not exit the electrode 260 and flow out of the catheter. Instead, the irrigating fluid stays completely within the catheter and is typically re-circulated. Thus, the same fluid may be used over and over again to cool the electrode 260.

Figure 3:
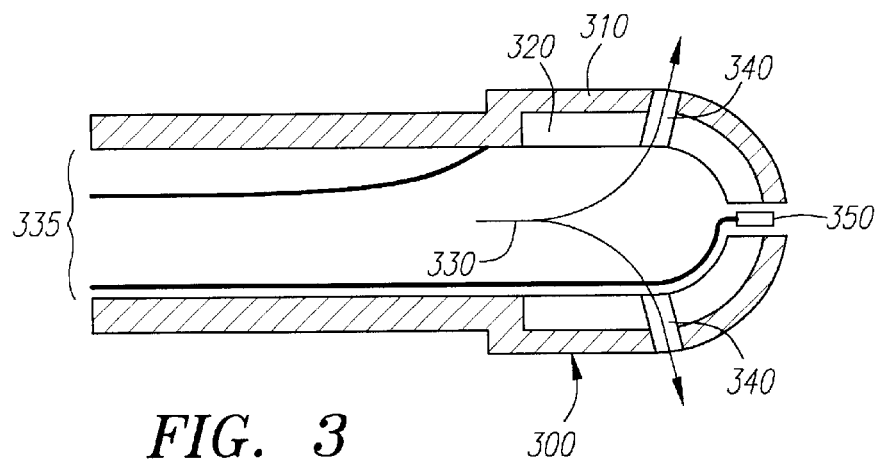
FIG. 3 is a cross-sectional view of a flushing irrigating catheter tip electrode comprising a biologically compatible outer layer and a thermally conductive inner layer.

Referring now to FIG. 3, another embodiment of the present invention is illustrated. In FIG. 3, a catheter is shown with a "flushing irrigation" catheter tip electrode 300 comprising a biologically compatible outer layer 310 and a thermally conductive inner layer 320 similar to the catheter tip electrode of FIG. 2. Unlike the electrode of FIG. 2, however, no irrigation channel runs through the inner layer 320. Rather, the irrigation fluid flows through an irrigation channel 335 formed by the inner surface of the inner layer 320 (where the RF wire and steering mechanism is typically situated) and exit out of exit ports 340, which extend through both the inner layer 320 and outer layer 310. Thus, the exit ports 340 provide an exit for the irrigation fluid flowing through the irrigation channel 335 via flow path 330. Again, a sensor 350, such as a thermistor, may be located at the distal end of the tip and the irrigation channel 335 may contain a 3D sensor (not shown).

Preferably, the walls of the irrigation channel 335 and/or exit ports 340 are covered by a layer of biologically compatible material, to ensure that there will be no adverse interaction between the highly conductive inner layer 320 (which is not biocompatible) and the cooling fluid, as well as any biological fluids and/or tissues, present in the irrigation channel 335 and exit ports 340.

The present invention, as embodied in FIG. 3, allows the excess heat in the outer layer 310 and in the outside space (which typically comprises of blood and tissue) immediately adjacent to the outer layer 310, to be dissipated through the inner layer 320 and into the irrigating fluid as it flows through the irrigation channel 335 and exits the exit ports 340. Upon exiting the exit ports 340, the irrigating fluid will mix with the body fluid (e.g., blood) in the surrounding outside space.

The electrode 300 described in FIG. 3 is one type of "flushing irrigation" catheter and is commonly referred to as a "showerhead" catheter tip electrode. The highly thermal conductivity inner layer 320 again has the benefits as described in reference to the embodiment of FIG. 2. In this case it is further advantageous for the patient, since the inner layer 320 allows the use of less irrigating fluid, thereby minimizing the fluid that enters the patient's body.

Figure 4A:
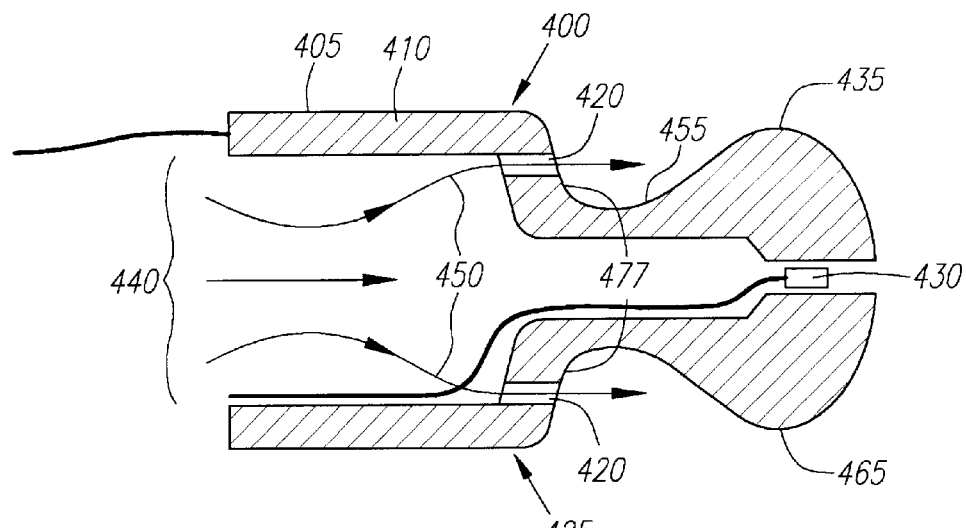
FIGS. 4A and 4B are cross-sectional views of self-cooling catheter tip electrodes, wherein the external surfaces of the electrodes are cooled by irrigation exit ports.

Other showerhead tip designs are also contemplated by the present invention and are described below. Referring to FIG. 4A, a catheter tip electrode 425 that "cools itself" is provided. The electrode 425 comprises a housing 410 composed essentially of a biologically compatible material, such as a platinum-iridium alloy. Alternatively, the housing 410 can be formed of a highly thermally conductive inner layer and a biologically compatible outer layer, much like the electrodes shown in FIGS. 2 and 3. Of course, the housing 410 may also be formed of both a highly conductive and biologically compatible (e.g., gold), in which case there would be no need to cover such a material with a biologically compatible material.

The housing 410 comprises a proximal section 405 and a distal section 435. The proximal section 405 comprises an irrigation channel 440 and a distally facing surface 455. The distal section 435 is mushroom-shaped, i.e., it comprises a neck 455 and head 465. The electrode 400 comprises irrigation exit ports 420, which extend through the distally facing surface 455 of the proximal section 405. Thus, an irrigating fluid, for example, a saline solution, flows through the irrigation channel 440 via flow path 450 and exits the electrode 400 through exit ports 420 proximal the distal end 435. As the irrigating fluid flows through the irrigation channel 440, the irrigating fluid takes away the thermal energy being dissipated from the housing 410. As the irrigating fluid exits the electrode 400 it is directed to flow over the head 465 of the distal section 435 to "cool itself." At the distal end of the electrode 400 is a sensor 430, for example, a thermistor or a thermocouple, which is in thermal contact with the electrode tip 160.

Figure 4B:
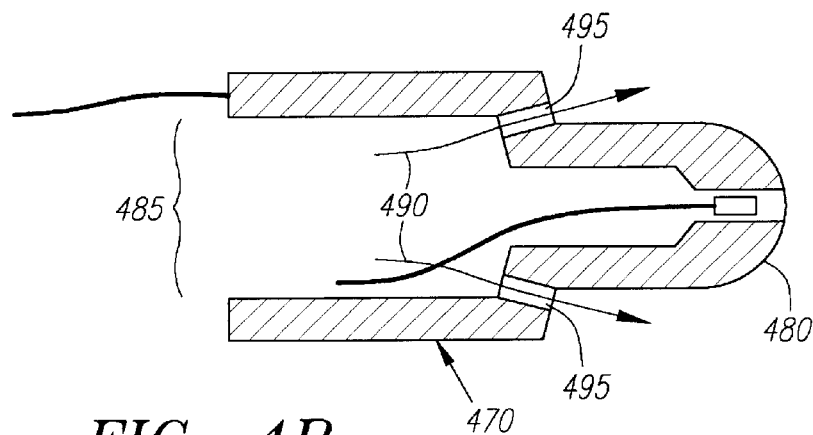

Alternatively, a catheter tip electrode 470 may be shaped such that a distal section 480 is straight rather than mushroom-shaped, as illustrated in FIG. 4B. The electrode 470 comprises a proximal section 475 with an irrigation channel 485 and a substantially distally facing surface 477. Thus, an irrigating fluid, for example, a saline solution, flows through an irrigation channel 485 via flow path 490 and exits the electrode 470 through exit ports 495 extending through the distally facing surface 477 proximal the distal end 480. As the irrigating fluid exits the electrode 470, it is directed to flow over the straight distal end 480 to "cool itself."

Figure 5:
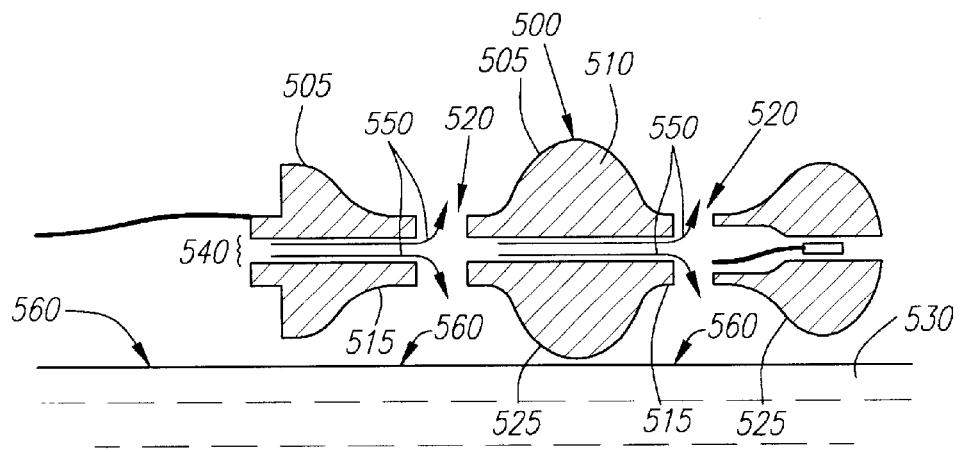
FIG. 5 is a cross-sectional view of a tissue-cooling catheter tip electrode, wherein the external surface comprises concave regions with irrigation exit ports for cooling surrounding tissue.

Referring now to FIG. 5, a catheter tip electrode 500 that "cools the surrounding tissue" is provided. This is achieved by forming the electrode 500 with an undulating outer surface 505, i.e., alternating between convex sections 525 and concave sections 515. The electrode 500 comprises a housing 510 composed essentially of a biologically compatible material, such as a platinum-iridium alloy. Alternatively, the housing 510 can be formed of a highly thermally conductive inner layer and a biologically compatible outer layer, much like the electrodes shown in FIGS. 2 and 3. Of course, the housing 510 may also be formed of both a highly conductive and biologically compatible (e.g., gold), in which case there would be no need to cover such a material with a biologically compatible material.

In any case, the irrigating fluid flows through the irrigation channel 540 via flow paths 550 and exits the electrode 500 through exit ports 520 in the concave sections 515 of the tip housing 510. As the irrigating fluid exits the electrode 500 it cools the surrounding tissues 530, e.g., at cooling areas 560. Thus, cooling fluid that may otherwise be blocked by direct tissue contact when using a level irrigated catheter tip, is delivered to the pertinent tissue substantially unimpeded.

Figure 6:
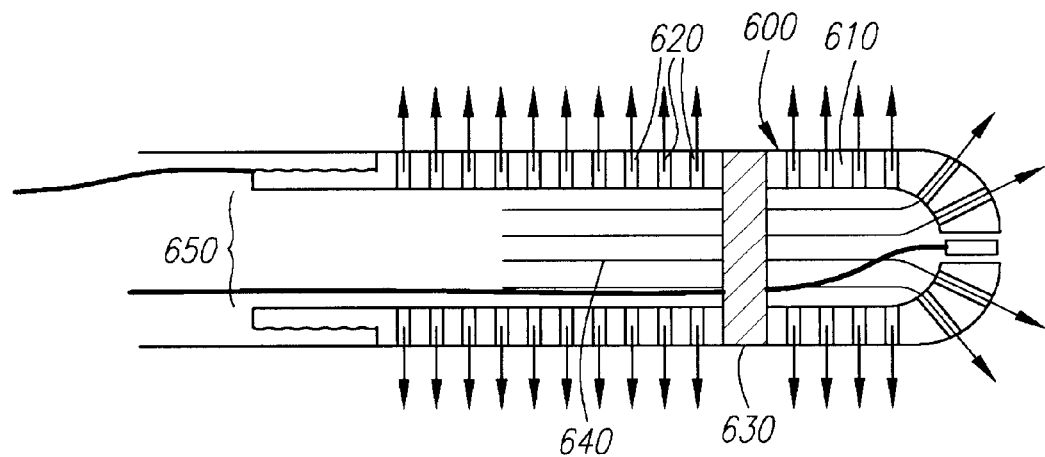
FIG. 6 is a cross-sectional view of a tissue-cooling catheter tip electrode comprising multiple irrigation exit ports.

Referring to FIG. 6, another catheter tip electrode 600 comprises a housing 610 made of a non-conductive material, e.g., plastic, that preferably withstand tissue temperatures without deforming. The housing 610 comprises a large number of irrigation exit ports 620 to provide sufficient cooling. Of course, the tip housing 610 may comprise a composite tip with a highly thermal conductive core (e.g., inner layer) covered by a biological compatible material. This tip housing 610 design, however, may be comprised entirely of biologically compatible material, since sufficient cooling is obtained through the use of a plethora of exit ports 620 in the housing 610. That is, an irrigating fluid flows through the irrigation channel 650 via flow paths 640 and exits the catheter through the exit ports 620 in the housing 610. The large number of exit ports 620 allows for reduced irrigation fluid flow and higher irrigation fluid temperature. This embodiment may also include a ring electrode 630 disposed around the housing 610, so that mapping may occur. Using this catheter tip design, the cooling liquid could be used as the source of RF energy that is applied to the tissue during ablation procedures.

Figure 7:
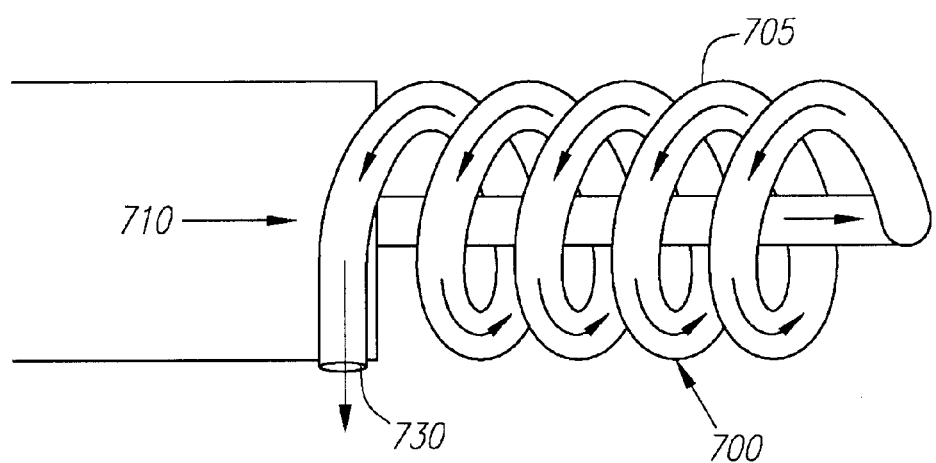
FIG. 7 a side view of a spiral shaped catheter tip electrode.

Referring to FIG. 7, a catheter tip electrode 700 comprises a spiral shape irrigation tube 705 composed essentially of biologically compatible material, such as a platinum-iridium alloy. Alternatively, the irrigation tube 705 can be formed of a highly thermally conductive inner layer and a biologically compatible outer layer, much like the electrodes shown in FIGS. 2 and 3. Of course, the irrigation tube 705 may also be formed of both a highly conductive and biologically compatible (e.g., gold), in which case there would be no need to cover such a material with a biologically compatible material.

The irrigating fluid flows through a passage 710 in the spiral irrigation tube 705 and exits the electrode 700 out through exit port 730, thereby cooling the inner surface of the tube 705. The wall of the spiral irrigation tube 705 is thin, thereby allowing the cooling fluid to run along a path closer to the surface of the electrode 700, causing greater cooling than an electrode cooled more towards the inner part thereof. Thus, the spherical design of this embodiment provides a larger cooling surface area resulting in improved cooling efficiency.

Figure 8:
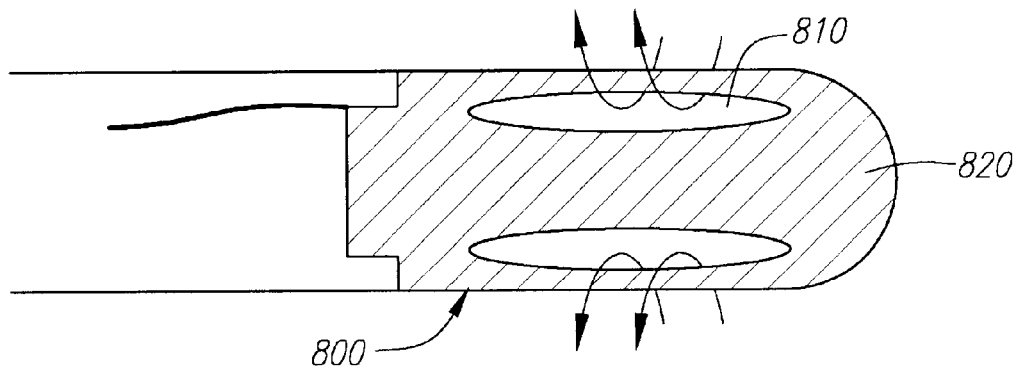
FIG. 8 is a cross-sectional view of a catheter tip electrode with flow-through channels.

Although in FIG. 7 the irrigating fluid is shown to be exiting through the outlet 730, the fluid does not have to exit the electrode 700. Rather, the cooling fluid may be re-circulated by directing the outlet 730 back through the catheter tubing to a pump. That is, the electrode 700 may be configured as an internally irrigated tip. Further, the shape of the spiral may vary (e.g., spacing between loops) and the cross-section of the hollow channel can also vary (e.g., circular, oval, etc.). Referring to FIG. 8, another embodiment having a catheter design with improved catheter tip cooling will be described. In this design, an electrode 800 comprises a tip housing 820 with "flow through" channels 810. Unlike the previously disclosed electrode designs, the flow through channels 810 of the catheter in FIG. 8 are not connected to an internal irrigation channel, but rather is a through channel for the external fluids (e.g., blood) to flow through. As such, the electrode cooling is accomplished in a first instance by the natural circulation of the surrounding fluid (i.e., blood). Alternatively, this embodiment could be combined with one or more of the other embodiments for even more enhanced tip cooling by internally circulating an irrigating fluid. For example, the tip housing 820 may comprise a thermally conductive core covered by a biological compatible material (not shown), such that the thermally conductive core is not in direct contact with the surrounding biological liquid and/or tissue. Of course, if the conductive core is biologically compatible, a biologically compatible material need not be used to cover the core. In any case, the electrode 800 is designed such that the through channels (or passageways) increase the surface area of the electrode 800, allowing for quicker cooling.

Figure 9:
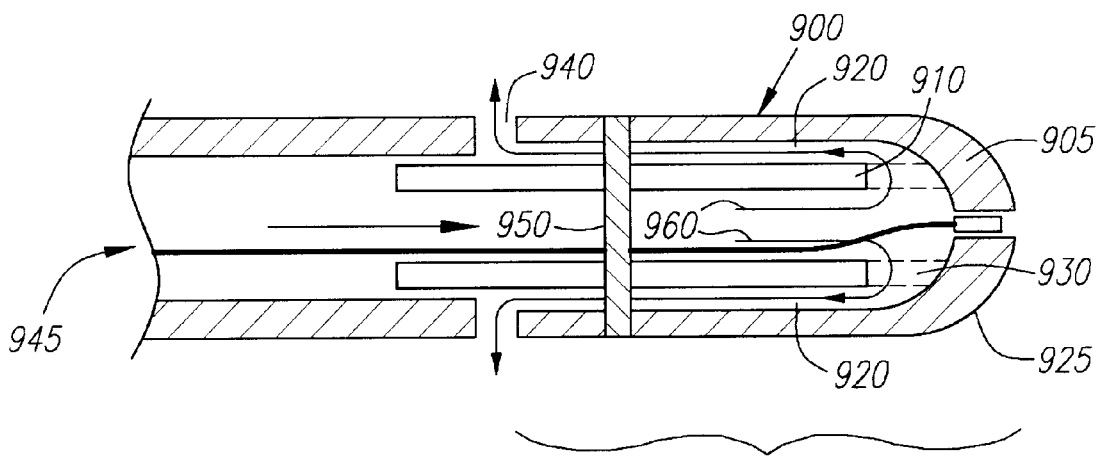
FIG. 9 is a cross-sectional view of a catheter tip electrode with an outer cap and an inner cylinder forming an annular irrigation channel therebetween.

Referring now to FIG. 9, yet another embodiment for an improved cooling of a catheter tip electrode 900 is provided. In this design, the irrigating fluid exits from an exit port 940, which is located at the proximal end of the electrode 900, rather than through exit ports located at the distal end. The electrode 900 comprises an inner cylinder and a concentrically overlapping outer cap 905, which are attached together by a pin 950 that extends laterally therethrough. Thus, an annular entry port 930 is formed between a distal end 925 of the outer cap 905 and the distal end of the inner cylinder 910, and an annular channel 920, which is in fluid communication with the annular channel 920, is formed between the inner surface of the outer cap 905 and the outer surface of the inner cylinder 910. It should be noted that the outer cap 905 and inner cylinder 910 may overlap anywhere in region 915, such that the channel 920 is formed. Following flow path 960, the irrigating fluid enters the electrode 900 from a proximal irrigation channel 945 within the inner cylinder 910 and flows towards the distal end 925 of the outer cap 905, where it enters into the annular entry port 930, through the annular channel 920, and out the exit ports 940. As a result, the electrode 900 is cooled.

The outer cap 905 is composed essentially of biologically compatible material, such as a platinum-iridium alloy. Alternatively, the outer cap 905 is formed of a highly thermally conductive inner layer and a biologically compatible outer layer, much like the electrodes shown in FIGS. 2 and 3. Of course, the outer cap 905 may also be formed of both a highly conductive and biologically compatible (e.g., gold), in which case there would be no need to cover such a material with a biologically compatible material.

Figure 10:
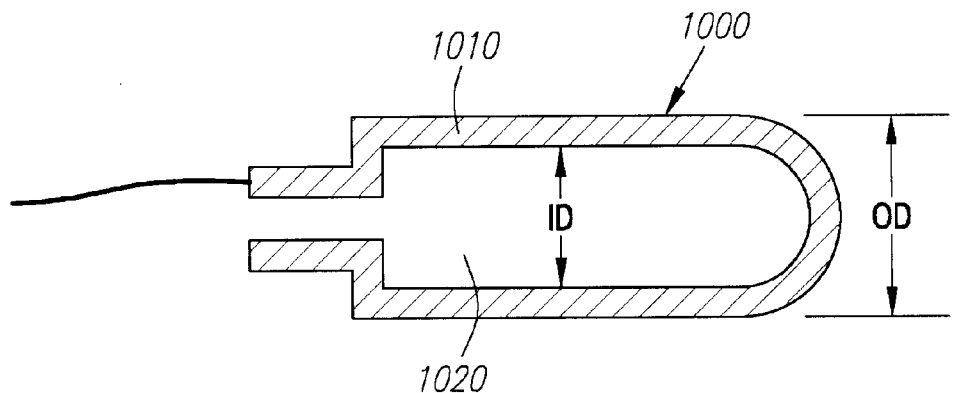
FIG. 10 is a cross-sectional view of a "thin-walled" catheter tip electrode.

Referring to FIG. 10, yet another embodiment for an improved cooled catheter tip electrode 1000 is shown. In this design, the walls of the electrode 1000 are thinned to improve the cooling rate of the electrode during irrigated procedures. The electrode 1000 includes a housing 1010 having an irrigation channel 1020. The housing 1010 has an inner diameter (ID) defined by its inner surface, and an outer diameter (OD) defined by its outer surface. Thus, the wall thickness of the housing 1010 can be defined as t=(OD−ID)/2. In the preferred embodiment, the wall of the housing 1010 is considered "thin-walled," which for the purposes of this specification is an ablation electrode, each wall of which exhibits a thickness t that is less than ID/2. Preferably the wall thickness t of the housing 1010 is less than ID/4 and more preferably less than ID/10. Thus, the cooling effects of irrigating fluid flowing through the electrode 1000 will be greater than that for electrodes that are not "thin-walled."

Specifically, the heat rate of conduction through a cylindrical wall can be described by the following equation:

$$q=(2\pi L k^* \Delta T)(ln(r_2/r_1)),$$

where L=length, k=thermal conductivity, ΔT=difference in temperature across the wall of the cylinder, $r_1$=ID/2, and $r_2$=OD/2. In comparing the heat rate of conduction between a conventional electrode, which typically has an ID and OD of 0.050 and 0.105 inches, respectively (i.e., $r_1$=0.025" and $r_2$=0.0525") with exemplary ID and OD values of the electrode 1000 of 0.08750 and 0.105 inches, respectively (i.e., $r_1$=0.04375" and $r_2$=0.0525), the increase in heat rate between the conventional electrode and the electrode 1000 (equal to $[1/ln(r_2/r_1)]_{new}/ln(r_2/r_1)]_{conv}$) is 4.069 greater. As a result, the electrode 1000 is capable of producing larger volume lesion than conventional electrodes.

Although particular embodiments of the present invention have been shown and described, it will be understood that it is not intended to limit the invention to the preferred embodiments and it will be obvious to those skilled in the art that various changes and modifications may be made without departing from the spirit and scope of the present invention. Thus, the invention is intended to cover alternatives, modifications, and equivalents, which may be included within the spirit and scope of the invention as defined by the claims.

What is claimed is:

1. A medical ablation electrode, comprising:

a biologically compatible outer layer of an electrically conductive material;

a thermally conductive inner layer; and an irrigation channel in contact with said inner layer for channeling cooling fluid.

2. The electrode of claim 1, wherein said outer layer is platinum iridium alloy.

3. The electrode of claim 2, wherein said platinum iridium alloy is composed of approximately 90 percent platinum and 10 percent iridium.

4. The electrode of claim 3, wherein said inner layer is copper.

5. The electrode of claim 1, wherein said outer layer is plated onto said inner layer.

6. The electrode of claim 1, wherein said inner layer is in contact with said outer layer, whereby said inner layer dissipates heat from said outer layer to fluid flowing through said irrigation channel.

7. The electrode of claim 1, wherein said irrigation channel is formed through said inner layer.

8. The electrode of claim 1, wherein an inner surface of said inner layer forms said irrigation channel.

9. The electrode of claim 1, further comprising an irrigation exit port extending laterally through said inner and outer layers, said exit port being in fluid communication with said irrigation channel.

10. The electrode of claim 9, wherein said irrigation channel comprises a wall that is covered by a layer of a biologically compatible material.

11. The electrode of claim 1, further comprising a RF ablation wire electrically coupled to said inner layer.

12. A medical ablation electrode, comprising:

a biologically compatible outer layer of an electrically conductive material;

a thermally conductive inner layer; and an irrigation channel formed within and extending along said inner layer for channeling cooling fluid.

13. The electrode of claim 12, wherein said outer layer is platinum iridium alloy.

14. The electrode of claim 13, wherein said platinum iridium alloy is composed of approximately 90 percent platinum and 10 percent iridium.

15. The electrode of claim 14, wherein said inner layer is copper.

16. The electrode of claim 12, wherein said inner layer is in contact with said outer layer, whereby said inner layer dissipates heat from said outer layer to fluid flowing through said irrigation channel.

17. The electrode of claim 12, further comprising a RF ablation wire electrically coupled to said inner layer.

18. A medical ablation electrode, comprising:

a biologically compatible outer layer of an electrically conductive material and exhibiting a first thermal conductivity;

a thermally conductive inner layer exhibiting a second thermal conductivity greater than said first thermal conductivity; and an irrigation channel in contact with said inner layer for channeling cooling fluid.

19. The electrode of claim 18, wherein said outer layer is platinum iridium alloy.

20. The electrode of claim 19, wherein said platinum iridium alloy is composed of approximately 90 percent platinum and 10 percent iridium.

21. The electrode of claim 20, said inner layer is copper.

22. The electrode of claim 18, wherein said inner layer is in contact with said outer layer, whereby said inner layer dissipates heat from said outer layer to fluid flowing through said irrigation, channel.

23. The electrode of claim 18, further comprising an irrigation exit port extending laterally through said inner and outer layers, said exit port being in fluid communication with said irrigation channel.

24. The electrode of claim 23, wherein said irrigation channel comprises a wall that is covered by a layer of a biologically compatible material.

25. The electrode of claim 18, further comprising a RF ablation wire electrically coupled to said inner layer.

* * * * *

UNITED STATES PATENT AND TRADEMARK OFFICE
CERTIFICATE OF CORRECTION

PATENT NO.     : 6,611,699 B2
DATED          : August 26, 2003
INVENTOR(S)    : Katie Krueger It is certified that error appears in the above-identified patent and that said Letters Patent is hereby corrected as shown below:

<u>Title page,</u>
Item [75], Inventors, delete "Katie Messing" and insert therefore -- Katie Krueger --

Signed and Sealed this

Thirteenth Day of April, 2004

JON W. DUDAS
*Acting Director of the United States Patent and Trademark Office*